US00PP19623P3

(12) United States Plant Patent
Meyer

(10) Patent No.: US PP19,623 P3
(45) Date of Patent: Jan. 13, 2009

(54) *HOSTA* PLANT NAMED 'BLUE IVORY'

(50) Latin Name: ***Hosta* sp.**
Varietal Denomination: Blue Ivory

(75) Inventor: William J. Meyer, Willingboro, NJ (US)

(73) Assignees: Lucas Klinkhamer, Hillegom (NL); Walters Gardens Inc., Zeeland, MI (US)

( * ) Notice: Subject to any disclaimer, the term of this patent is extended or adjusted under 35 U.S.C. 154(b) by 110 days.

(21) Appl. No.: 11/716,857

(22) Filed: Mar. 12, 2007

(65) Prior Publication Data

US 2008/0229460 P1 Sep. 18, 2008

(51) Int. Cl.
*A01H 5/00* (2006.01)

(52) U.S. Cl. ..... Plt./353
(58) Field of Classification Search ..... Plt./353
See application file for complete search history.

(56) References Cited

PUBLICATIONS

Internet website; http://www.hostaparadise.com/nwdetails2.aspx?HostaID=2011 (1 page total).*

* cited by examiner

*Primary Examiner*—S. B. McCormick-Ewoldt

(57) ABSTRACT

A new and distinct *Hosta* plant named 'Blue Ivory' characterized by elliptic to cordate leaves having wide light creamy-colored margins and blue-green centers, vertical flower scapes with medium lavender flowers above foliage, suitable for landscape, potted culture, or cut flower arrangements.

2 Drawing Sheets

Botanical classification: *Hosta* sp.
Variety denomination: 'Blue Ivory'.

CROSS-REFERENCE TO RELATED PLANTS

The most similar known hosta cultivars are: 'First Frost' (not patented). 'El Niño' (U.S. Plant Pat. No. 14,632), 'Sleeping Beauty' (not patented), 'Aristocrat' (U.S. Plant Pat. No. 11,286), and 'Tambourine' (not patented). H. 'First Frost', 'El Niño', and 'Sleeping Beauty' are all cream to white margined sports of 'Halcyon', however 'Blue Ivory' has a margin nearly twice as wide. 'Blue Ivory' also is whiter in the margin than 'First Frost'. 'Aristocrat' has more cordate or rounded leaves with thinner margins, and tends to be shorter habit. 'Tambourine' is an offspring of 'Halcyon' with a narrower more yellow creamy margin, has darker purple flowers, is slightly larger in habit and has more green and less blue leaf centers than 'Blue Ivory'.

BACKGROUND AND ORIGIN OF THE PLANT

The present invention relates to the new and distinct hosta plant, *Hosta,* 'Blue Ivory' discovered by William J. Meyer in the summer of 2003 at a nursery in Eastern Connecticut. The plant is an un-induced whole plant sport of the *Hosta* cultivar 'Halcyon' (not patented). 'Halcyon' was a first generation cross of *Hosta tardiflora*×*Hosta sieboldiana* (Tardiana Group) by Eric Smith, of England. The plant has been successfully propagated by tissue culture methods at a plant nursery in Rijswik, The Netherlands and found to produce identical plants that maintain the unique characteristics of the original plant. The plant is stable and reproduces true to type in successive generations of asexual reproduction.

SUMMARY OF THE PLANT

*Hosta* 'Blue Ivory' differs from its parent, 'Halcyon', as well as all other hostas known to the applicant, in that the plant has a very wide variegated leaf margin that emerges pale yellow to cream in the spring and with sunlight and warmer temperatures lightens to a white with an occasional slight frosting of green in some areas of the white margin. The leaf center is a blue green. There are over 3,600 cultivars registered with The American Hosta Society, which is the International Cultivar Registration Authority for the genus *Hosta. Hosta* 'Blue Ivory' differs from these and all unregistered cultivars known to the inventor in that it has:

1. Intense, long-lasting blue green foliage margined with a very wide creamy white border;
2. Compact habit, medium sized clumps with flower scapes above foliage enough for each medium lavender flower to be effectively displayed.

BRIEF DESCRIPTION OF THE DRAWINGS

The photographs of the new plant demonstrate the overall appearance of the plant, including the unique traits. The colors are as accurate as reasonably possible with color reproductions. Ambient light spectrum, source and direction may cause the appearance of minor variation in color.

DETAILED BOTANICAL DESCRIPTION

Figure 1:
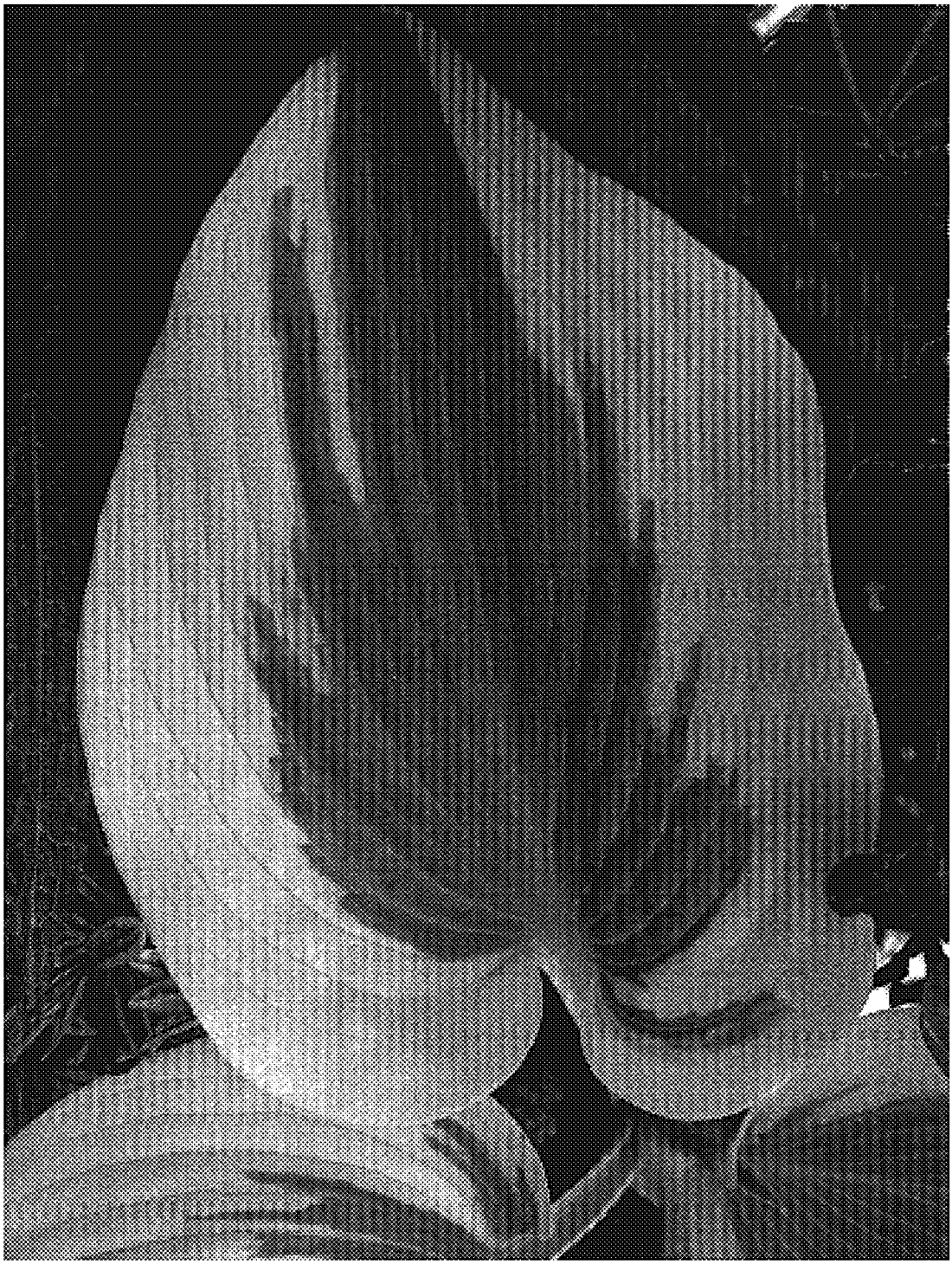
FIG. 1 shows the foliage early in the season in Rijswik, Netherlands.
Figure 2:
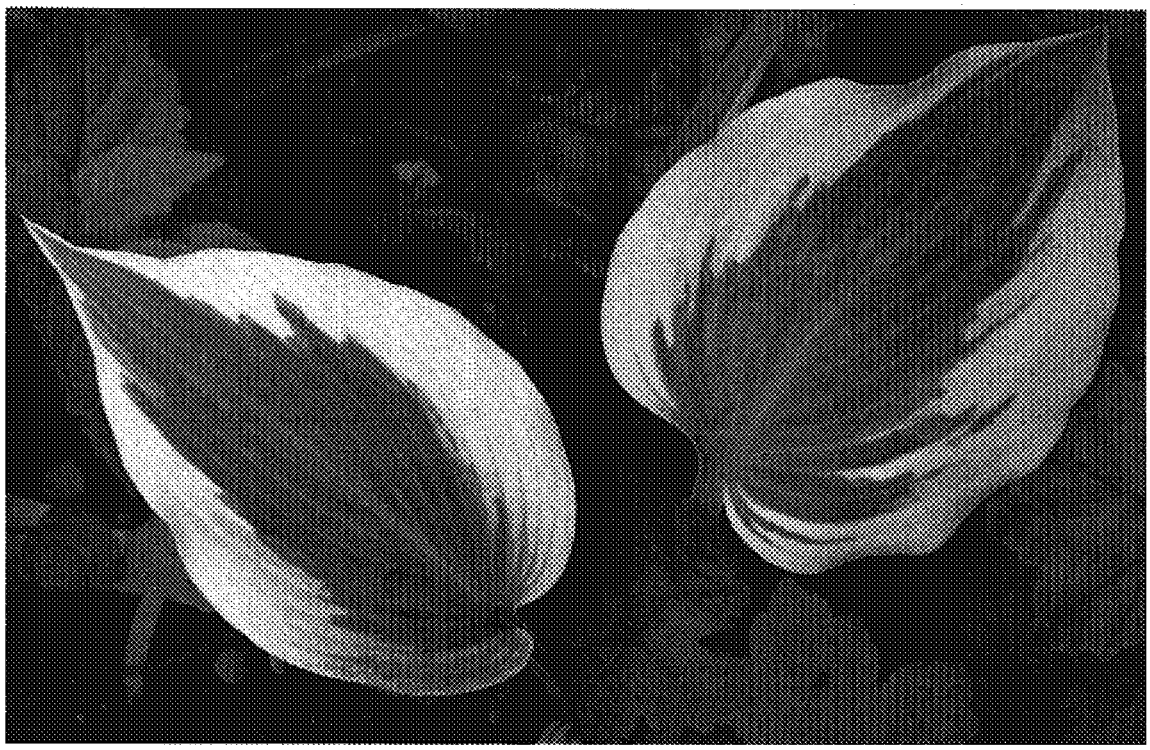
FIG. 2 shows the foliage in mid July in Willingboro, N.J., USA.

The following descriptions and color references are based on the 2001 edition of The Royal Horticultural Society Colour Chart except where common dictionary terms are used. The new plant, *Hosta* 'Blue Ivory' has not been observed under all possible environments. The phenotype may vary slightly with different environmental conditions, such as temperature, light, fertility, moisture and maturity levels, but without any change in the genotype. The following observations and size descriptions are of a two-year old plant in a garden in Willingboro, N.J. under open high tree shade canopy with supplemental water and fertilizer.

Botanical classification: *Hosta* sp.

Parentage: Naturally occurring sport of *Hosta* 'Halcyon' (not patented).

*Propagation method.*—By sterile laboratory tissue culture division and garden division.

*Time to initiate roots from tissue culture.*—about three weeks.

*Rooting habit.*—Normal, fleshy, lightly branching.

Plant description:

*Plant shape and habit.*—Hardy herbaceous perennial with basal rosette leaves, symmetrical and arching over, spreading by rhizomes.

*Crop time.*—Summer growing 15 to 20 weeks to finish in a one-liter container; vigor is good.

*Plant size.*—foliage height at flowering is about 25 cm tall from soil line to the top of the leaves and about 30 cm wide at soil line.

Foliage description: Elliptic to cordate leaf blades 12 to 16 cm long, 7 to 8 cm wide, average 14 cm long by 7 cm wide, symmetrical; acute apex and rounded base; entire margin; variegation pattern on the white edge varies in different regions of the leaf from 5 to 25 mm wide, average of 20 mm; 9 to 11 pairs of major parallel veins; top surface is smooth except for slight indentations for major veins, dull with heavy glaucous bloom, and bottom surface also is dull and has heavy glaucous bloom; petiole 10 to 14 cm long, 7 to 10 mm wide, average 12 cm long and 9 cm wide.

*Blade color of young emerging leaf.*—adaxial (top) margin: between RHS 4B and RHS 4C; center RHS 141B; abaxial (underside) margin: RHS 4C; center RHS 141B or RHS 141C; some intermediate colors on top and bottom with the major portion between RHS N 144A and RHS N144C.

*Blade color of mature leaves.*—adaxial (top) center. RHS 122A; margin: near white, lighter than RHS 155D with occasional green frosting mixed with white of RHS 138B and RHS 141C; the major intermediate portions are RHS 144C and RHS 122C; abaxial (underside) center: between RHS 122A and RHS 119A; margin near white, whiter than RHS 155D. Veins color is the same as the surrounding leaf tissue on both the top and bottom of the leaf in the margins and slightly lighter in the center.

*Petioles.*—15 to 20 cm long and 10 to 14 mm wide. The leaf margin continues down the petiole 1 to 2 mm wide and RHS 4 C on young foliage on both top and back, and center is nearest RHS 145 A on both surfaces. On older foliage the petiole margin of both surfaces is RHS 4 D, and the center gradually lightens on both surfaces going toward middle to RHS 119 C.

Flower description:

*Buds.*—One day prior to opening between RHS 76B and RHS 76 C; approximately 4.5 cm long, up to 1.5 cm wide, clavate with acute apex and longer thin base.

*Flowers.*—20 to 28 per scape; funnelform; 2.5 to 2.8 cm wide and 4.5 to 5.0 cm long, (distal flowers being smaller), persists for a normal period, usually one day on or cut from plant; scapes remain effective from mid July into mid August; no detectable fragrance.

*Tepal.*—Two sets of three fused at the base; clavate with acute apex; entire; approximately 4 cm long and 1.4 cm wide; coloring of both sets identical; RHS 76 C on the outside; inside between RHS 77 C and RHS 77D. Both sets of tepals have white margins on entire inside.

*Gynoecium.*—Single; Style — 5.5 to 5.8 cm long, white, 1 mm diameter, curled at distal end, Stigma — 1 mm to 2 mm in diameter, white.

*Androecium.*—Filaments — six, white, less than 1 mm in diameter and 5.0 cm long; Anthers — 4 mm long, 1.0 mm wide, RHS 79 A.

*Pollen.*—Elliptical, less than 0.1 mm long, nearest RHS 15 A.

*Bracts.*—Lower bracts before flowers sessile with acute apex, protruding upward about 30 degree angle away from scape; lowest up to 4 cm long and 1.5 cm wide before first flower, center RHS 143 C, with the margin near white; bracts subtending flowers protrude less than 90 degrees; initial bracts about 3.0 to 4.0 cm long and 1.0 cm wide, center RHS 145 B, margin RHS N138 B with frosting of RHS 186 B throughout.

*Peduncle.*—One per mature division; glaucous, erect 35 to 45 cm tall, and up to 8 mm in diameter, light bluish green color RHS 119 B mid section and lightening to RHS N138 D.

*Pedicel.*—Approximately 0.6 cm long, 2 mm wide, RHS 138 C.

*Fruit and seed.*—Have not yet been observed.

Disease resistance: Resistance beyond that of other hostas has not been observed. The plant grows best with plenty of moisture and adequate drainage, but is able to tolerate some drought when mature. Hardiness at least from USDA zone 3 through 9, and other disease resistance is typical of that of other hostas.

I claim:

1. A new and distinct cultivar of ornamental *Hosta* plant named 'Blue Ivory' as herein described and illustrated, with elliptic to cordate leaves having wide light creamy-colored margins and blue-green centers, suitable as a potted plant, for the garden, and for cut flower arrangements.

* * * * *